United States Patent [19]

O'Brien

[11] Patent Number: 4,896,959

[45] Date of Patent: Jan. 30, 1990

[54] VISUAL ACUITY UNIT FOR TREATMENT OF AMBLYPIA

[75] Inventor: Richard W. O'Brien, Philadelphia, Pa.

[73] Assignee: Visual Enhancement, Inc., Philadelphia, Pa.

[21] Appl. No.: 120,877

[22] Filed: Nov. 6, 1987

Related U.S. Application Data

[63] Continuation-in-part of Ser. No. 36,205, May 4, 1979, Pat. No. 4,726,672, which is a continuation of Ser. No. 771,703, Sep. 3, 1985, abandoned.

[51] Int. Cl.⁴ ............................................... G61B 3/00
[52] U.S. Cl. ..................................... 351/203; 351/222
[58] Field of Search ............... 351/203, 226, 200, 201, 351/222, 223, 224

[56] References Cited

U.S. PATENT DOCUMENTS

| | | | |
|---|---|---|---|
| 3,421,498 | 1/1969 | Gans | 351/226 |
| 3,883,234 | 5/1975 | Lynn et al. | 351/226 |
| 4,239,351 | 12/1980 | Williams et al. | 351/226 |
| 4,294,522 | 10/1981 | Jacobs | 351/203 |
| 4,353,626 | 10/1982 | Harrison | 351/203 |
| 4,408,846 | 10/1983 | Balliet | 351/203 |
| 4,533,221 | 8/1985 | Trachtman | 351/203 |

OTHER PUBLICATIONS

Video Games and Amblyopia Treatment; Shippman 35 American Orthoptic Journal 2, (1985).

Primary Examiner—Rodney B. Bovernick
Assistant Examiner—P. M. Dzierzynski
Attorney, Agent, or Firm—Ferrill and Logan

[57] ABSTRACT

The present invention provides improved apparatus for treatment of amblyopia and similar eye conditions through use of a solitary visual target maintained at a level of minimal discernible size. The improved apparatus provides instantaneous electronic switching between targets of different acuity demand levels, compact optics requiring limited case size, and automatic scoring of correct responses.

20 Claims, 4 Drawing Sheets

VISUAL ACUITY UNIT FOR TREATMENT OF AMBLYPIA

This is a continuation-in-part of copending U.S. patent application Ser. No. 036,205, U.S. Pat. No. 4,726,672 filed 05-04-1979, which was a continuation of application Ser. No. 771,703 filed 09-03-1985, now abandoned.

BACKGROUND OF THE INVENTION

The present invention relates to apparatus for treating amblyopia and similar eye conditions caused by a lack of acuity which is not of a refractive or transparent nature.

As is explained in the copending application, it has been found that amblyopia can be treated, with a significant increase in acuity, using apparatus which isolates the affected eye, presents a solitary visual target of minimum discernible size, and forces the subject to focus on and identify figures displayed on the target. The treatment is simple and easy, requiring merely five minutes, twice a day. In each case, examination of the subject's eyes demonstrates that the improvement in acuity is not a function of refractive or transparent changes in the subject's eye. This basic apparatus using a lighted target was employed both in a large darkened room, and contained in a darkened case using two mirrors and a lens to expand the optical distance within a contracted space.

Although this method and basic apparatus achieved remarkable results, the apparatus itself was deficient in a number of respects. The use of only a single solitary target required the target to be physically moved each time the acuity level had to be changed. With use of the unit contained in a case, this required opening the case, readjusting or changing the target and the lens to one of many predetermined locations, each location providing a particular acuity level, and then reassemblying the apparatus. This usually amounted to far too complicated a procedure to provide treatment at multiple acuity levels during a single treatment. Additionally, many people, particularly young children, have great difficulty correctly changing the lens and target locations. A further problem with the basic apparatus is that it did not make optimum use of space, thus creating a somewhat unwieldy package to transport, store, and use. Finally, the basic apparatus provided minimum feedback to the user, requiring the user to keep track of the number of correct and incorrect responses he had during a given session.

In light of the above considerations, it is a primary object of the present invention to provide improved apparatus for treatment of amblyopia and similar eye conditions which can be easily and rapidly switched between various levels of acuity demand.

It is a further object of the present invention to provide an acuity therapy unit which provides a full range of acuity demands within a compact and easily portable case.

It is an additional object of the present invention to provide an acuity therapy unit which tallies the responses of a user and provides a read-out of the number of correct responses given during a session.

SUMMARY OF THE INVENTION

The present invention provides improved apparatus for treatment of amblyopia and similar eye conditions through use of a solitary visual target of minimal discernible size, presented free from all visual interferences, and requiring a user to view and identify a figure shown thereon.

The apparatus of the present invention employs multiple lighted visual targets, each set at a different acuity demand level and each to be viewed solitarily, and electronic switching between the targets. Each time the unit is used, a user simply chooses which of the targets is at his threshold of visibility and performs treatment at that level—increasing or decreasing the acuity demand as necessary. Significant improvement in nonrefractive acuity has been demonstrated with merely five minutes of treatment, twice a day. Additional improvements include electronic scoring of answers and improved optical arrangement to significantly reduce the size of the case of the unit.

The benefits of the present invention include: instantaneous switching of acuity demand, thus assuring that the solitary target is always maintained at its minimal discernible size without undue strain to the user or the need to stop treatment to reset the target; instantaneous scoring of responses, again limiting the non-treatment demands on the subject; and compacting the optics and electronics into a selfcontained, easily portable, case.

DETAILED DESCRIPTION OF THE INVENTION

Copending U.S. patent application Ser. No. 036,205, now allowed, explains that successful treatment of non-refractive acuity problems, such as amblyopia, can be accomplished by visually isolating a subject and presenting for observation a solitary visual target of minimum size. The target should be presented free from all other visual interference. By having the subject repeatedly observe barely readable figures displayed on the target and identify them, it has been found that nonrefractive acuity can increase dramatically, even in amblyopic subjects who have failed at years of conventional patch treatment. Crucial to such treatment is the ability to maintain the target in a position that the steadily improving acuity of the subject can barely discern. The present invention provides improved apparatus to accomplish such treatment.

Figure 1:
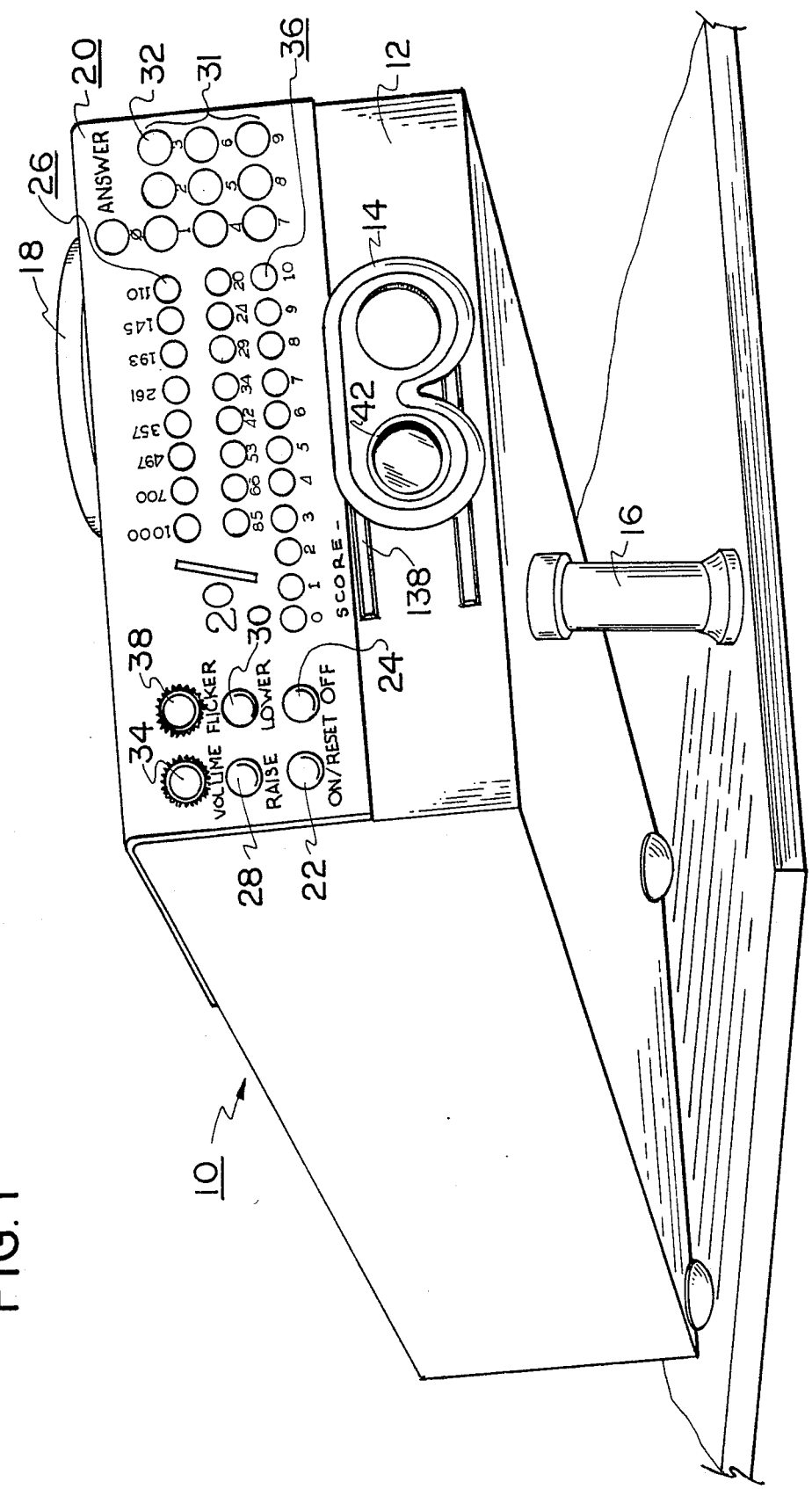
FIG. 1 is a three-quarter view of the exterior of a case containing the present invention.

The improved acuity therapy unit 10 of the present invention is shown in FIG. 1. The unit 10 comprises a contained, ambient light excluding, case 12; a mask 14 through which a user interfaces with the interior of the case 12; an adjustable (or interchangeable) monoped stand 16 which threads into the case 12 and supports the unit 10 in a comfortable operating position for table top use; a battery compartment (not shown); a speaker 18, and a control panel 20. As is fully explained below, the interior of the unit 10 contains sixteen discrete visual targets (not shown) ranging in acuity demand (i.e. Snellen denominator) from 20/1000 to 20/20.

The control panel 20 contains all the controls necessary for operating the unit 10 and making all adjustments in acuity demand. The unit 10 is turned on, reset, or turned off using on/reset switch 22 and off switch 24, respectively. The acuity demand of the target presently displayed is shown by illumination of one of the sixteen discrete light emitting diode (LED) Snellen denominator indicator lights 26. In order to increase or decrease the acuity demand of the target, the user merely presses either the raise button 28 or lower button 30.

In the present embodiment, the figures displayed on the visual targets are numbers 0 through 9. Upon identifying a number, the user enters his response on keyboard 31 by pressing one of the ten answer buttons 32. An audible "correct" or "incorrect" tone is then provided on the speaker 18. The volume of the tone can be controlled by rheostat knob 34.

The electronic circuitry of the present invention automatically tallies every ten answers given by the user and, at the end of ten responses, provides a score on one of ten discrete LED score lights 36.

It has been found that having the target flicker between a number and its inverse (e.g. on a seven-segment LED display, the inverse of the number "0" is "−") greatly increases and maintains the interest level of the user. Accordingly, a rheostat knob 38 has been provided to adjust the rate of flicker.

It should be noted that although distinct LEDs have been used for indicator lights 26 and score lights 36, any other form of display can be readily substituted, including a digital readout, without departing from the intent of the present invention.

Figure 2:
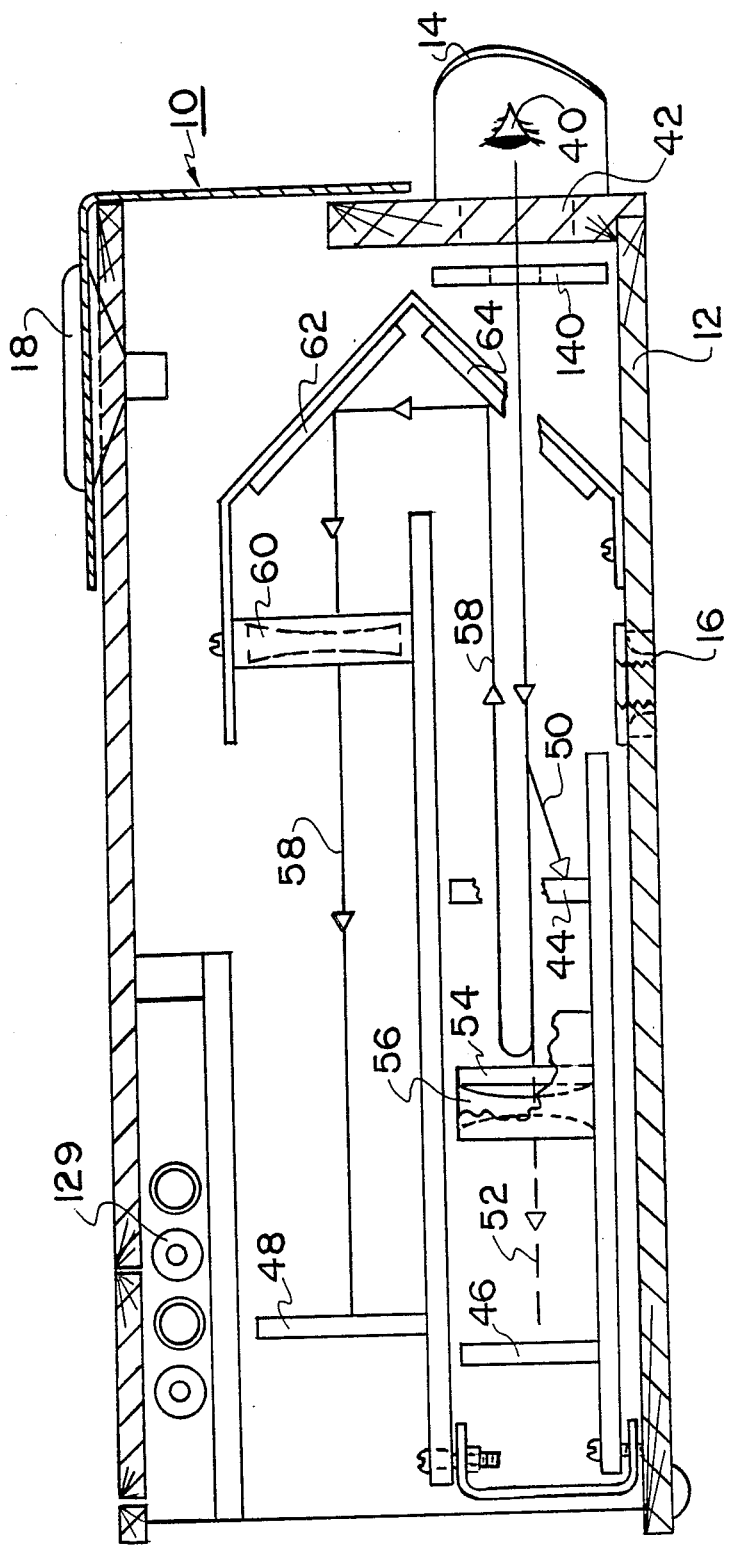
FIG. 2 is a side sectional view of the optical apparatus of the present invention.

The internal optics of the present invention are shown in FIG. 2. The user interfaces with the unit 10 by positioning his affected eye 40 before an opening 42 in case 12. Ambient light is excluded from the case, and the user is sequestered from lateral distraction, by use of mask 14. It is preferred that the interior of the case be provided with a black matte finish to further lessen the reflection of light in the case.

The interior of the case contains multiple visual targets, each set at a distinct acuity demand level. In the preferred embodiment, sixteen targets are provided. As is explained below, the electronics of the present invention will illuminate only one of sixteen targets at a time. This presents a single lighted target floating in a black void. Naturally, when only one target is lit, no other targets or their reflections will be seen. The visual targets are divided into three target clusters 44, 46, and 48.

Cluster 44 is directly viewed by the user along visual path 50. By using conventional light emitting diode (LED) displays of heights 20.32 mm, 14.22 mm, 10.9 mm, and 7.62 mm, the user will be confronted with images at acuity demands of 20/1000, 20/700, 20/497, and 20/357, respectively. It is believed that at these levels of extremely poor acuity, the user is virtually unable to accommodate and so the targets need not be placed within the viewer's accommodation range (i.e. beyond ten inches of the user). Cluster 44 should be oriented to one side to avoid interference with the images from the other clusters.

As the acuity of the user improves, he can move to the targets of cluster 46. These targets are viewed along visual path 52 through a partially reflective mirror or "beam splitter" 54 and a lens 56. Using a lens with a focal length of −61 mm, to decrease the apparent size of the targets, and LED targets of heights 20.32 mm, 14.22 mm, 10.9 mm, 9.19 mm, and 6.86 mm, the user will be confronted with images at acuity demands 20/261, 20/193, 20/145, 20/110, and 20/85, respectively. Again, it is believed that at these acuity levels, accommodation demand is not critical.

As the acuity of the user continues to improve, he should move to the targets of cluster 48. These targets are viewed along visual path 58. Visual path 58 passes through lens 60 and reflects off mirrors 62 and 64, and beam splitter 54. Using a lens with a focal length of −52 mm and LED targets of heights 25.9 mm, 20.32 mm, 16.0 mm, 12.7 mm, 10.9 mm, 9.19 mm, and 7.62 mm, the user will be confronted with images at acuity demands 20/66, 20/53, 20/42, 20/34, 20/29, 20/24, and 20/20, respectively. At these acuity levels, accommodation demand is somewhat of a concern and the virtual image of cluster 48 should be positioned approximately forty inches from the user. Additionally, where a user has trouble accommodating, correction with glasses may be necessary.

It must be noted that any combination of individually lighted visual targets and mirrors, beam splitters and/or lenses may be employed to accomplish the same effect of presenting a series of solitary visual targets at comfortable intervals of acuity demands. A lighted liquid crystal display or an array of light emitting diodes arranged in a matrix display, either one of which may be capable of presenting multiple targets of various sizes and electronic switching between such targets, may also be suitable.

Figure 3:
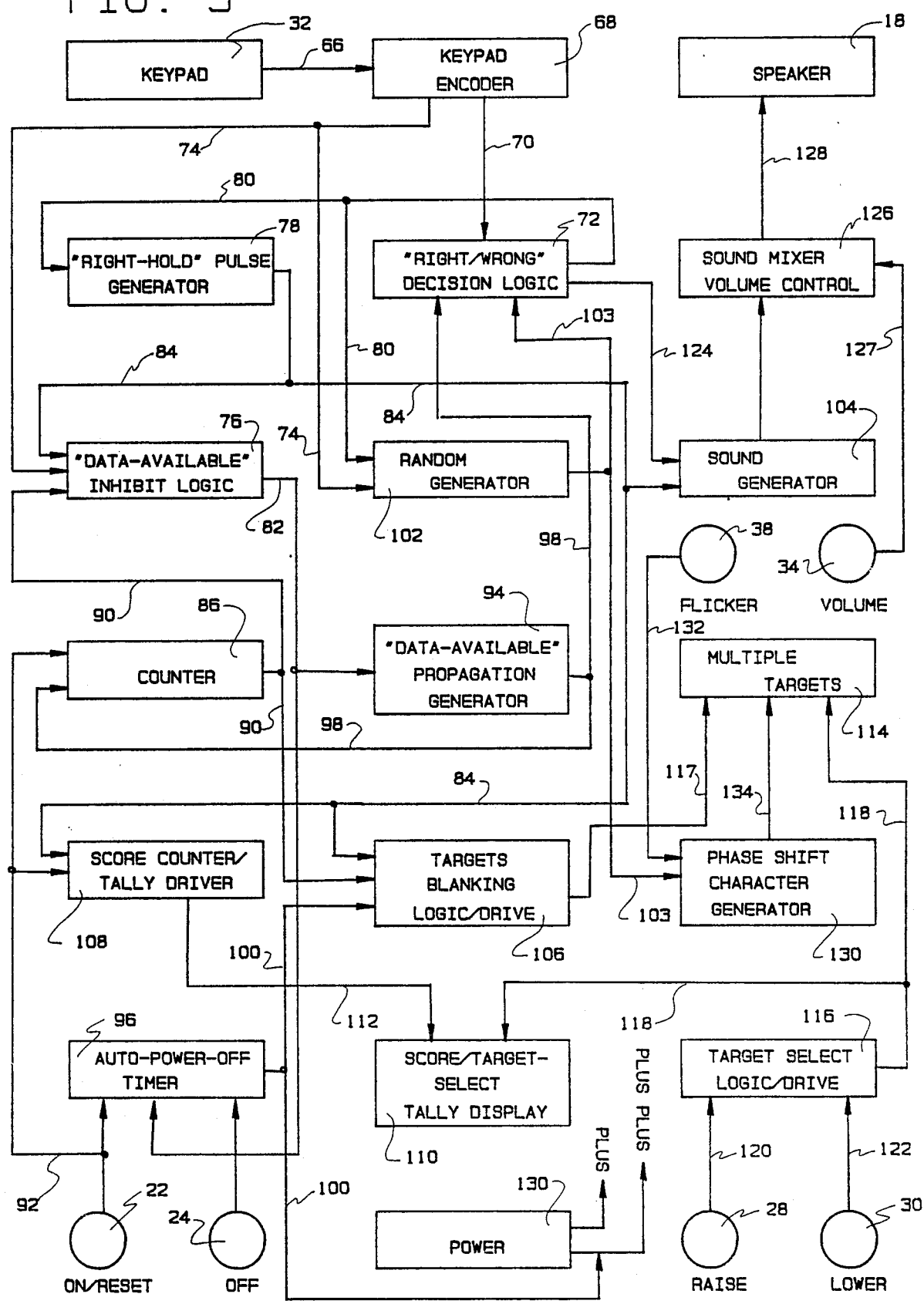
FIG. 3 is a schematic representation of the electronics employed in the present invention.

The enabling electronics of the present invention are schematically set forth in FIG. 3. The keypad 32 consists of ten answer buttons 31 wired in a 3 line by 4 line matrix. The output of this matrix is fed over line 66 to a keypad encoder 68, such as a type 74C922 keypad encoder. The output of the keypad encoder 68 is fed over line 70 to a right/wrong decision logic 72.

The right/wrong decision logic 72 comprises: a comparator, such as a type 74HC85 comparator; a "right" gate, such as a type 74HC00 2-input NAND gate; and a "wrong" gate, such as a type 74HC00 2-input NAND gate. The purpose of these gates is to inhibit right/wrong decision logic 72 output when none of the buttons 31 are pressed. The keypad encoder 68 also outputs a data-available signal over line 74 to data-available inhibit logic 76 which comprises a 3-input NAND function, such as a type 74HC10 3-input NAND gate.

A right-hold pulse generator 78 is provided which is driven over line 80 by the right/wrong decision logic 72 when the right/wrong decision logic 72 senses a "right" subject answer condition. While a correct answer key 32 is pressed, the output of data-available inhibit logic 76 over line 82 is inhibited by the right-hold pulse generator 78 via a signal over line 84.

A ten-tries counter 86 is provided, comprising a counter, such as a type 74HC393 counter. The function of the counter 86 is to count user answer entries into blocks of ten. The output of the counter 86 drives data-available inhibit logic 76 over line 90. The counter 86 will inhibit the data-available signal over line 82 when it has reached a count of ten user answer tries entered into keypad 32 and will hold this inhibit condition until the counter 86 is reset by the on/reset button 22 over line 92. The data-available signal over line 74, if passed by the data-available inhibit logic 76, will feed over line 82 to a data-available propagation corrector 94. Line 82 also feeds an auto-power-off timer 96.

The data-available propagation corrector 94 comprises a one-shot multivibrator, such as a type 74HC423 monostable multivibrator. The function of the data-available propagation corrector 94 is to inhibit the first few milliseconds of the data-available pulse which appears on line 82. The output of the data-available propagation corrector 94 feeds the "right" gate and the "wrong" gate of the right/wrong decision logic 72 over line 98. These gates inhibit a "right" output or a "wrong" output of the right/wrong decision logic 72 in response to data available inhibit logic 76.

The auto-power-off timer 96 comprises: an up/down counter, such as a type 74HC193 up/down counter; a clock, such as a CMOS type TLC 556CN; and a gate, such as a type 74HC10 3-input NAND gate. The on/reset button 22 resets the counter to a count of zero. The off button 24 resets the counter to a count of fifteen. The gate senses a count of fourteen or a count of fifteen. Upon sensing a count of fourteen or fifteen the gate drives a device, such as a transistor, to shut-down the main power of the unit 10 over line 100. The data-available propagation corrector 94 output over line 98 increments by one the counter 86.

A random generator 102 is provided to produce the figures to be displayed at random. The random generator comprises: a one-shot multivibrator, such as a type 74HC423 multivibrator; a clock, such as a TLC 556CN; and a counter, such as a type 74HC192 up/down counter. The "right" output of the right/wrong decision logic over line 80 enables the multivibrator of the random generator 102. During the pulse of the multivibrator, the clock is forced into oscillation and the counter counts pulses of this oscillation. To enhance randomness, the data available signal from the keypad encoder 68 is fed to the multivibrator over line 74 to chop the pulse of the multivibrator upon the release of an answer button 32 by a user. The output of the random generator 102 enters the "right/wrong" decision logic 72 via line 103 for comparison with the user's answers received over line 70.

The right-hold pulse generator 78 is triggered over line 80 by a "right" output of the right/wrong decision logic 72. In turn, the right-hold pulse generator 78 via line 84: commands a sound generator 104 to generate a "right" sound for the duration of the right-hold pulse; commands targets blanking logic/drive 106 to blank all targets; and drives the score counter/tally driver 108 to increment its count by one.

The right-hold pulse generator 78 comprises a multivibrator, such as CMOS type TLC 556CN. The score/target-select tally display 110 consists of the discrete LEDs of score lights 36 and acuity indicator lights 26. The score counter/tally driver 108 comprises a counter, such as a type 74HC393 counter and a demultiplexer, such as a type 74HC154 demultiplexer. The output of the demultiplexer drives the discrete LEDs of the score lights 36 of the score/target-select tally display 110 over line 112. Hence the score lights 36 of the score/target-select tally display 110 will indicate the current "right" count of the score counter/tally driver 108.

Target blanking logic/drive 106 comprises an "OR" gate function, such as a 74HC10 gate, and a control device such as a positive-negative-positive transistor. Additional blanking commands to target blanking logic/drive 106 comes from counter 86 over line 90 and from auto-power-off timer 96 over line 100.

As has been discussed above, the command from the counter 86 occurs as the count of counter 86 reaches ten and will hold until the counter 86 is reset to zero by the on/reset pushbutton 22 over line 92. The command from the auto-power-off timer 96 will cause blanking to occur as the counter counts fourteen or fifteen and will hold until the auto-power-off timer 96 is reset to zero by on/reset button 22 over line 92.

As has been explained, the multiple targets 114 comprise the three clusters 44, 46, and 48, totalling sixteen visual targets. The "current" figure to be displayed is received over line 103 from the random generator 102 via a character generator. Target select logic/drive 116 selects one of multiple targets 114 via signals over line 118. The user selects the desired target of multiple targets 118 by a command over line 120 generated by the "raise" button 28 or a command over line 122 generated by the "lower" button 30.

The target select logic/drive 116 comprises: an up/down counter, such as a type 74HC193 counter; a "raise" one-shot multivibrator, such as a type 74HC423A multivibrator, for pushbutton 28 de-bounce; and a "lower" one-shot multivibrator, such as a type 74HC423A multivibrator, again for pushbutton 30 de-bounce. Target select logic/drive 116 drives the acuity demand indicator lights 26 of the score/target-select tally display 110 over line 118. Hence the score/target-select tally display 110 will indicate the target currently selected by the target select logic/drive 116. The multiple targets 114 will blank if an appropriate signal is received from target blanking logic/drive 106 over line 117.

The right/wrong decision logic 72 drives the sound generator 104 over line 124 to cause the "wrong" sound to occur during a "wrong" keypress if permitted by the data-available signal over line 98. The sound generator 104 comprises two astable multivibrators, such as CMOS type TLC 556CN. The sound mixer/volume control 126 may be a resistive mixing network, and a potentiometer controlled by rheostat knob 34 over line 127. The mixer 126 then powers speaker 18 via line 128.

Power 130 may consist of any power source, although, due to the small power drain of the system, battery power 129 is preferred, as shown in FIG. 2. Power 130 has two outputs: plus and plus-plus. Some circuitry, such as the auto-power-off timer 96, is fed by plus and is never shut off; the remaining circuitry is fed by plus-plus which is controlled by the auto-power-off timer 14 over line 100.

As has been discussed, a phase shift character generator 130 may be employed to increase user interest. The character generator 130 receives the "current" figure to be displayed from the random generator 102 over line 103. The generator 130 may comprise: a seven segment decoder, such as a type 74HC411 triple 3-input AND gate; seven exclusive OR gates, such as type 74HC86 exclusive OR gates; and a clock, such as a TLC 556CN. Clock frequency, or "flicker rate," is controlled by a potentiometer controlled by rheostat knob 38 over line 132. All segments of the "current" target will flicker on and off per the clock frequency. The seven segment decoder will cause phase shifting of desired elements per the exclusive OR gates. Hence information is injected into the multiple targets 114 over line 134 via phase shifting.

As is shown in FIGS. 1 and 2, the unit 10 may be readily adapted for right or left eye treatment through one of at least two simple modifications. As is shown in FIG. 1, the mask 14 may be mounted on a sliding track 138 which permits the user to center either his right or left eye over a single common opening 42 in the case 12. Alternatively, dual openings 42 can be provided with a reversible slat 14, containing a single opening, positioned inside the case 12. The entire optical chassis of the unit 10 must then be shifted to accommodate either a right or left eye treatment. Although this latter embodiment is not preferred, it does permit factory customization of the unit 10 for particular users.

Figure 4:
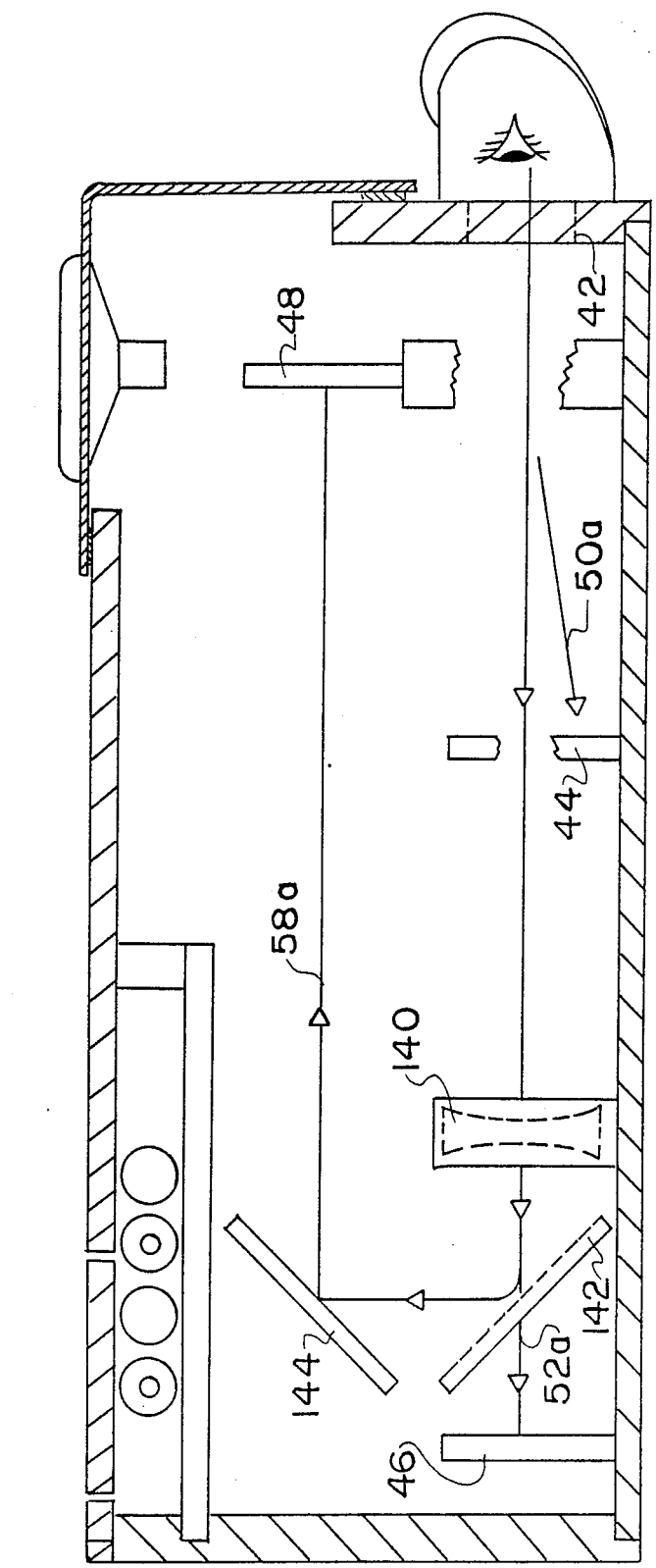
FIG. 4 is a side sectional view of another embodiment of the optical apparatus of the present invention.

FIG. 4 shows another optical embodiment of the present invention. Using the common opening 42 arrangement, the optical chassis may be greatly simplified while retaining the same target clusters 44, 46, and 48.

The user's view of cluster 44 remains the same over visual path 50a. However, visual paths 52a and 58a are somewhat modified. The view of cluster 46 is through a lens 140, of −52 mm focal length and a beam splitter 142 positioned at a 45-degree angle to visual path 52a. The view of cluster 48 is again through lens 140, and is reflected off beam splitter 142 and mirror 144.

This embodiment significantly reduces the optics needed to support the present invention and decreases slightly the size of case 12. In all other respects, it operates in the same manner as the first embodiment shown in FIGS. 1–3.

While particular embodiments of the present invention have been disclosed herein, it is not intended to limit the invention to such a disclosure and changes and modifications may be incorporated and embodied within the scope of the following claims.

What is claimed is:

1. In an ocular stimulator unit to improve a user's acuity having a solitary visual target presented without interference from other visual stimulus, means for randomly selecting and generating at least one of a number of various figures to be displayed on the target, a keyboard through which the user can respond to various figures seen on the visual target, means for comparing the displayed figure with responses from the keyboard, means to inform the user of the correctness or incorrectness of the response, and means to adjust the apparent size of the displayed figure to maintain the figure displayed at a level of minimal discernible size, the improvement which comprises wherein the means to adjust the apparent size of the displayed figure comprises multiple lighted visual targets, each target available to serve as the solitary visual target presented individually during treatment and without interference from the other targets;

wherein said multiple visual targets are placed in a darkened chamber;

means to maintain each of the visual targets at a different acuity demand level; and means for the user to select electronically which of the multiple targets to view.

2. The apparatus of claim 1 wherein the means to maintain each of the multiple targets at a different acuity level comprises at least two clusters of plural visual targets, each cluster containing targets of plural apparent sizes, wherein each cluster is oriented at a different optical distance from the user.

3. The apparatus of claim 2 wherein the apparent size of at least one of the targets is achieved in part through use of at least one lens.

4. The apparatus of claim 2 wherein the optical distance between the user and at least one cluster is achieved in part through use of at least one reflective surface.

5. The apparatus of claim 4 wherein at least one of the reflective surfaces is a beam splitter.

6. The apparatus of claim 5 wherein a cluster of visual targets is positioned behind the beam splitter, the targets therein to be viewed through said beam splitter, and another cluster of visual targets is positioned in front of the beam splitter, the reflection of the targets therein to be viewed on the beam splitter.

7. The apparatus of claim 2 wherein said plural visual targets are achieved through use of a single display capable of generating figures of multiple sizes.

8. The apparatus of claim 1 wherein the means for the user to select electronically which of the multiple targets to view comprises each target being a light emitting diode (LED) display;

each LED display being powered from a common source;

target select logic being provided to direct power to only one LED display; and means being provided to control which display is to be illuminated.

9. The apparatus of claim 8 wherein the target select logic comprises an up/down counter and a demultiplexer connected between the power source and each of the displays.

10. The apparatus of claim 1 wherein the means to inform the user of the correctness or incorrectness of the response includes means to tally the user's correct responses.

11. The apparatus of claim 10 wherein said tallying means comprises a counter receiving a signal for each correct response connected to a demultiplexer, the output of the demultiplexer driving a display showing the number of correct responses.

12. A user controlled acuity therapy unit for treatment of amblyopia and similar conditions, which unit comprises:

a darkened chamber;

multiple lighted visual targets placed in the darkened chamber, each target to be viewed alone without interference of other visual stimulus;

means for randomly selecting and generating at least one of a number of various figures to be displayed on a target;

a keyboard through which the user can respond to various figures seen on a visual target;

means for comparing the displayed figure with responses from the keyboard;

means to inform the user of the correctness or incorrectness of a response;

means to maintain each of the targets at a different acuity level; and means for the user to select electronically which of the multiple targets to view in order to maintain the figure displayed thereon at a level of minimal discernible size.

13. The apparatus in accordance with claim 12 wherein the means to maintain each of the targets at a different acuity level comprises dividing the multiple visual targets into at least two clusters of plural visual targets, each cluster of plural targets containing targets of plural apparent sizes; and positioning each cluster at a different optical distance from the user.

14. The apparatus in accordance with claim 13 wherein the apparent size of at least one target is altered by using at least one lens.

15. The apparatus in accordance with claim 13 wherein the optical distance between a cluster and the user may be increased within a chamber of restricted size through use of at least one reflective surface.

16. The apparatus in accordance with claim 15 wherein at least one of the reflective surfaces is a beam splitter.

17. The apparatus in accordance with claim 16 wherein at least one cluster of visual targets is positioned behind the beam splitter, the targets therein viewed through said beam splitter; and at least one other cluster of visual targets is positioned in front of the beam splitter, the reflection of the targets therein viewed on the beam splitter.

18. The apparatus of claim 12 wherein the means for the user to select electronically which of the multiple targets to view comprises
a target select logic which controls which one of the lighted targets is to be illuminated; and
means to direct said target select logic to illuminated specific target.

19. The apparatus of claim 18 wherein the target select logic comprises an up/down counter and a demultiplexer connected between a power source and each of the displays.

20. The apparatus of claim 12 wherein the means to inform the user of the correctness or incorrectness of a response includes tallying means comprising a counter receiving a signal for each correct response connected to a demultiplexer, the output of the demultiplexer driving a display showing the number of correct responses.

* * * * *